US009717697B2

(12) United States Patent
Liao et al.

(10) Patent No.: US 9,717,697 B2
(45) Date of Patent: Aug. 1, 2017

(54) COMPOSITIONS AND METHODS FOR THE TRANSDERMAL DELIVERY OF METHYLPHENIDATE

(71) Applicant: Noven Pharmaceuticals, Inc., Miami, FL (US)

(72) Inventors: Jun Liao, Miami, FL (US); Puchun Liu, Miami, FL (US); Steven Dinh, Miami, FL (US)

(73) Assignee: Noven Pharmaceuticals, Inc., Miami, FL (US)

(*) Notice: Subject to any disclaimer, the term of this patent is extended or adjusted under 35 U.S.C. 154(b) by 0 days.

(21) Appl. No.: 14/052,190

(22) Filed: Oct. 11, 2013

(65) Prior Publication Data

US 2014/0105979 A1    Apr. 17, 2014

Related U.S. Application Data

(60) Provisional application No. 61/713,893, filed on Oct. 15, 2012, provisional application No. 61/785,325, filed on Mar. 14, 2013.

(51) Int. Cl.
*A61K 9/70* (2006.01)
*A61K 31/4458* (2006.01)

(52) U.S. Cl.
CPC ........ *A61K 9/7061* (2013.01); *A61K 31/4458* (2013.01)

(58) Field of Classification Search
None
See application file for complete search history.

(56) References Cited

U.S. PATENT DOCUMENTS

| | | |
|---|---|---|
| 2,838,519 A | 6/1958 | Rometsch et al. |
| 5,064,654 A | 11/1991 | Berner et al. |
| 5,234,957 A | 8/1993 | Mantelle et al. |
| 5,332,576 A | 7/1994 | Mantelle et al. |
| 5,446,070 A | 8/1995 | Mantelle et al. |
| 5,474,783 A | 12/1995 | Miranda et al. |
| 5,656,286 A | 8/1997 | Miranda et al. |
| 5,719,197 A | 2/1998 | Mantelle et al. |
| 5,958,446 A | 9/1999 | Miranda et al. |
| 6,024,974 A | 2/2000 | Li |
| 6,024,976 A | 2/2000 | Miranda et al. |
| 6,210,705 B1 | 4/2001 | Mantelle et al. |
| 6,221,383 B1 | 4/2001 | Miranda et al. |
| 6,235,306 B1 | 5/2001 | Miranda et al. |
| 6,316,022 B1 | 11/2001 | Mantelle et al. |
| 6,348,211 B1 | 2/2002 | Mantelle et al. |
| 7,993,671 B2 | 8/2011 | Mantelle et al. |
| 8,337,884 B2 | 12/2012 | Mantelle et al. |
| 8,632,802 B2 | 1/2014 | Kanios et al. |
| 8,715,723 B2 | 5/2014 | Kanios et al. |
| 2002/0102291 A1 | 8/2002 | Mantelle et al. |
| 2005/0169977 A1* | 8/2005 | Kanios et al. ............... 424/449 |
| 2006/0078604 A1* | 4/2006 | Kanios et al. ............... 424/449 |
| 2007/0059349 A1 | 3/2007 | Mantelle et al. |
| 2007/0071800 A1* | 3/2007 | Foreman et al. ............ 424/448 |
| 2008/0008746 A1 | 1/2008 | Mantelle et al. |
| 2011/0160245 A1 | 6/2011 | Mantelle et al. |
| 2011/0288124 A1 | 11/2011 | Mantelle et al. |
| 2014/0105979 A1 | 4/2014 | Liao et al. |
| 2014/0179739 A1 | 6/2014 | Mantelle et al. |

FOREIGN PATENT DOCUMENTS

WO    WO 02/24157 A2    3/2002

OTHER PUBLICATIONS

U.S. Appl. No. 14/206,298, filed Mar. 12, 2014, Liao.
U.S. Appl. No. 14/133,900, filed Dec. 19, 2013, Kanios et al.
Kanios et al., "Effect of Non-Functional/Non-Reactive Pressure Sensitive Adhesives in Transdermal Drug Delivery Systems," retrieved from the Internet: http://www.pstc.org/files/public/Kanios.pdf, retrieved on Nov. 8, 2013.
International Search Report issued on Dec. 18, 2013 in application No. PCT/US2013/064494.
Faraj et al., "Metabolism and Disposition of Methylphenidate-$^{14}$C: Studies in Man and Animals," J. Pharm. Exper. Ther., vol. 191, No. 3, pp. 535-547, 1974.
Physicians' Desk Reference, "Methylphenidate," 39$^{th}$ Edition, p. 865, 1985.

\* cited by examiner

*Primary Examiner* — David J Blanchard
*Assistant Examiner* — Daniel F Coughlin
(74) *Attorney, Agent, or Firm* — Foley & Lardner LLP

(57) ABSTRACT

Compositions for the transdermal delivery of methylphenidate in a flexible, finite form are described. The compositions comprise a polymer matrix that includes methylphenidate or a pharmaceutically acceptable salt and at least one acrylic polymer that is non-reactive with methylphenidate. Methods using the compositions to achieve transdermal delivery of methylphenidate or for treating Attention Deficit Disorder (ADD) and/or Attention Deficit/Hyperactivity Disorder (ADHD), postural orthostatic tachycardia syndrome, or narcolepsy also are described.

26 Claims, No Drawings

COMPOSITIONS AND METHODS FOR THE TRANSDERMAL DELIVERY OF METHYLPHENIDATE

RELATED APPLICATIONS

This application claims priority to U.S. provisional application 61/713,893, filed Oct. 15, 2012 and U.S. provisional application 61/785,325, filed Mar. 14, 2013, the entire contents of which are incorporated herein by reference in their entirety.

FIELD

The present invention relates generally to the transdermal delivery of methylphenidate, and to methods of transdermally delivering methylphenidate, such as may be desired for treating Attention Deficit Disorder (ADD) and/or Attention Deficit/Hyperactivity Disorder (ADHD), postural orthostatic tachycardia syndrome, or narcolepsy.

BACKGROUND

Many factors influence the design and performance of transdermal drug delivery compositions. These include the individual drugs themselves, the physical and chemical characteristics of the compositions' components and their performance and behavior relative to other components, external and environmental conditions during manufacturing and storage, properties of the application site, the desired rate of drug delivery and therapeutic onset, the desired drug delivery profile, and the intended duration of delivery, among others.

Compositions for the transdermal delivery of methylphenidate are known, but there remains a need for compositions that exhibit suitable physical and pharmacokinetic properties.

SUMMARY

In accordance with some embodiments, there are provided compositions for the transdermal delivery of methylphenidate in the form of a flexible finite system for topical application, comprising a polymer matrix consisting essentially of (a) methylphenidate or a pharmaceutically acceptable salt thereof; and (b) at least one acrylic polymer that is non-reactive with methylphenidate. In some embodiments, the polymer matrix consists essentially of a first non-reactive acrylic polymer and methylphenidate or pharmaceutically acceptable salt thereof. In some embodiments, the polymer matrix consists essentially of a first non-reactive acrylic polymer, a second non-reactive acrylic polymer, and, optionally, additional non-reactive acrylic polymers, and said methylphenidate or pharmaceutically acceptable salt thereof. In some embodiments, the non-reactive acrylic polymer(s) include one or more monomers selected from the group consisting of methyl acrylate, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, and amide group-containing monomers, such as and octyl acrylamide.

In accordance with any of these embodiments, at least one non-reactive acrylic polymer may include methyl acrylate and 2-ethylhexyl acrylate monomers. Additionally, or alternatively, at least one non-reactive acrylic polymer may include amide group-containing monomers. Additionally, or alternatively, at least one non-reactive acrylic polymer may include methyl methacrylate, 2-ethylhexyl acrylate, butyl acrylate monomers and amide group-containing monomers.

In accordance with specific embodiments, the polymer matrix consists essentially of (a) first non-reactive acrylic polymer that includes 50% methyl acrylate monomers and 50% 2-ethylhexyl acrylate monomers, based on the weight of the first acrylic polymer; (b) a second non-reactive acrylic polymer that includes methyl methacrylate monomers, 2-ethylhexyl acrylate monomers, butyl acrylate monomers, and amide group-containing monomers, and (c) methylphenidate or a pharmaceutically acceptable salt thereof.

In accordance with other specific embodiments, the polymer matrix consists essentially of (a) first non-reactive acrylic polymer that includes 80% methyl acrylate monomers and 20% 2-ethylhexyl acrylate monomers, based on the weight of the first acrylic polymer; (b) a second non-reactive acrylic polymer that includes methyl methacrylate monomers, 2-ethylhexyl acrylate monomers, butyl acrylate monomers and amide group-containing monomers and (c) methylphenidate or a pharmaceutically acceptable salt thereof.

In accordance with other specific embodiments, the polymer matrix consists essentially of (a) first non-reactive acrylic polymer that includes 80% methyl acrylate monomers and 20% 2-ethylhexyl acrylate monomers, based on the weight of the first acrylic polymer; (b) a second non-reactive acrylic polymer that includes 50% methyl acrylate monomers and 50% 2-ethylhexyl acrylate monomers, based on the weight of the second acrylic polymer and (c) methylphenidate or a pharmaceutically acceptable salt thereof.

In accordance with other specific embodiments, the polymer matrix consists essentially of (a) a non-reactive acrylic polymer that includes 80% methyl acrylate monomers and 20% 2-ethylhexyl acrylate monomers, based on the weight of the acrylic polymer and (b) methylphenidate or a pharmaceutically acceptable salt thereof.

In accordance with any embodiments, the polymer matrix may have a coat weight of about 4-7 mg/cm$^2$ based on the active surface area of the polymer matrix, such as a coat weight of about 6.6 mg/cm$^2$ or 5.5 mg/cm$^2$, based on the active surface area of the polymer matrix.

In accordance with any embodiments, the composition may have a methylphenidate content of about 0.5-3 mg/cm$^2$ based on the active surface area of the polymer matrix, such as a methylphenidate content of about 1.65 mg/cm$^2$ based on the active surface area of the polymer matrix, or a methylphenidate content of 20-30% by weight, based on the weight of the polymer matrix.

In accordance with any embodiments, the composition may deliver methylphenidate over a period of time of at least about 8-12 hours.

In accordance with other embodiments, there are provided methods of making the composition described herein.

In accordance with other embodiments, there are provided methods for the transdermal delivery of methylphenidate, or for treating Attention Deficit Disorder (ADD) and/or Attention Deficit/Hyperactivity Disorder (ADHD), or postural orthostatic tachycardia syndrome, or narcolepsy, comprising topically applying a composition as described herein to the skin or mucosa of a subject in need thereof.

In accordance with other embodiments, there are provided compositions as described herein for use in the transdermal delivery of methylphenidate, such as for use by topically application to the skin or mucosa of a subject in need thereof, or for use in treating Attention Deficit Disorder (ADD) and/or Attention Deficit/Hyperactivity Disorder (ADHD), postural orthostatic tachycardia syndrome, or narcolepsy.

DETAILED DESCRIPTION

Described herein are compositions and methods for the transdermal delivery of methylphenidate in a flexible, finite form (e.g., "patch"-type systems). The compositions comprise a polymer matrix that includes methylphenidate or a pharmaceutically acceptable salt thereof and at least one acrylic polymer that is non-reactive with methylphenidate. The compositions exhibit satisfactory physical properties while also achieving satisfactory pharmacokinetic profiles.

DEFINITIONS

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein means that the described composition (e.g., polymer matrix, etc.) comprises less than about 5%, less than about 3%, or less than about 1% by weight, based on the total weight of the composition at issue, of the excluded component(s).

As used herein "subject" denotes any mammal in need of drug therapy, including humans. For example, a subject may be suffering from or at risk of developing a condition that can be treated or prevented with methylphenidate (such as ADD or ADHD), or may be taking methylphenidate for health maintenance purposes.

As used herein, the terms "topical" and "topically" mean application to a skin or mucosal surface of a mammal, while the terms "transdermal" and "transdermal" connote passage through the skin or mucosa (including oral, buccal, nasal, rectal and vaginal mucosa), into systemic circulation. Thus, the compositions described herein may be applied topically to a subject to achieve transdermal delivery of methylphenidate.

As used herein, the phrases "therapeutically effective amount" and "therapeutic level" mean that drug dosage or plasma concentration in a subject, respectively, that provides the specific pharmacological effect for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

As used herein, "active surface area" means the surface area of the drug-containing polymer matrix of the transdermal drug delivery system.

The compositions described herein are in a "flexible, finite form." As used herein, the phrase "flexible, finite form" means a substantially solid form capable of conforming to a surface with which it comes into contact, and capable of maintaining contact so as to facilitate topical application. Such systems in general are known in the art and commercially available, such as transdermal drug delivery patches. The compositions comprise a drug-containing polymer matrix that releases an active agent (such as methylphenidate) upon application to the skin (or any other surface noted above). In some embodiments, the composition in flexible, finite form may include a backing layer and/or a release liner layer in addition to a drug-containing polymer matrix layer.

As used herein, "drug-containing polymer matrix" refers to a polymer composition which contains one or more drugs, such as methylphenidate, and a polymer, such as a pressure-sensitive adhesive polymer or a bioadhesive polymer. A polymer is an "adhesive" or "bioadhesive" if it has the properties of adhesiveness per se. Other polymers can function as an adhesive or bioadhesive by the addition of tackifiers, plasticizers, crosslinking agents, skin permeation enhancers, or other excipients. Thus, in some embodiments, the polymer optionally comprises tackifiers, plasticizers, crosslinking agents or other additives known in the art.

As used herein, the term "pressure-sensitive adhesive" refers to a viscoelastic material which adheres instantaneously to most substrates with the application of very slight pressure and remains permanently tacky. As noted above, a polymer is a pressure-sensitive adhesive polymer if it has the properties of a pressure-sensitive adhesive per se. Other polymers may function as a pressure-sensitive adhesive by admixture with tackifiers, plasticizers or other additives. The term pressure-sensitive adhesive also includes mixtures of different polymers.

As used herein, the term "non-reactive acrylic polymer" identifies acrylic polymers that do not contain functional groups with active hydrogen atoms or functional groups with hydrogen atoms available for chemical reaction or interaction with methylphenidate, such as, for example, carboxyl, hydroxyl, amine, thiol or silanol groups. As used herein, non-reactive acrylic polymers may include amide group-containing monomers (e.g., polymers with amido groups).

In some embodiments, the polymer matrix is a pressure-sensitive adhesive at room temperature and exhibits desirable physical properties, such as good adherence to skin, ability to be peeled or otherwise removed without substantial trauma to the skin, retention of tack with aging, etc.

In accordance with some embodiments, the compositions described herein comprise a polymer matrix that consists essentially of methylphenidate or a pharmaceutically acceptable salt thereof and at least one non-reactive acrylic polymer. In this context, the phrase "consists essentially of" means that the polymer matrix is substantially free of other polymer components, although it may include other excipients known to be useful in transdermal compositions (such as tackifiers, plasticizers, crosslinking agents or other excipients known in the art) as long as those other excipients do not degrade the physical or chemical properties of the compositions to pharmaceutically unacceptable levels. In some embodiments, the polymer matrix includes a penetration enhancer. In some embodiments, the polymer matrix does not include a penetration enhancer.

Methylphenidate

Methylphenidate (a-phenyl-2-piperidineacetic acid methyl ester) is a chiral drug. While commercially available methylphenidate products (such as the oral product Ritalin® and the transdermal product Daytrana®) include a 50:50 (racemic) mixture of d- and l-threo-methylphenidate, it is believed that the d-threo-methylphenidate isomer has greater pharmacological activity. The compositions described herein may be formulated with any isomer of methylphenidate, although compositions comprising a racemic mixture of d- and l-threo-methylphenidate, or comprising primarily the d-threo-methylphenidate isomer may be most commercially relevant.

The compositions described herein may be formulated with methylphenidate free base ("methylphenidate base"), any pharmaceutically acceptable salt thereof, or mixtures thereof. Exemplary suitable pharmaceutically acceptable salts of methylphenidate are salts of weak inorganic and organic acids, and quaternary ammonium salts. These include without limitation, salts with acids such as sulfuric, phosphoric, hydrochloric, hydrobromic, hydriodic, sulfamic, citric, lactic, maleic, malic, succinic, tartaric, cinnamic, acetic, benzoic, gluconic, or ascorbic acid, or quaternary ammonium salts with organic esters of sulfuric, hydrohalic, or aromatic sulfonic acids, such as methyl chloride, methyl bromide, ethyl chloride, propyl chloride, butyl chloride, isobutyl chloride, benzylchloride, benzyl bromide, phenethyl bromide, naphthylmethyl chloride, dimethyl sulfate, methyl benzenesulfonate, ethyl toluenesulfonate, ethylene chlorohydrin, propylene chlorohydrin, allyl bromide, methylallyl bromide or crotyl bromide esters.

The compositions described herein include a therapeutically effective amount of methylphenidate or pharmaceutically acceptable salt thereof. Generally, the amount of methylphenidate is from about 1% to about 50%, including from about 5% to about 40%, such as from about 10% to about 30% by weight, or from about 20% to about 30% by weight, based on the total dry weight of the polymer matrix. In specific embodiments, the polymer matrix comprises about 20% by weight methylphenidate, based on the total dry weight of the polymer matrix. In specific embodiments, the polymer matrix comprises about 25% by weight methylphenidate, based on the total dry weight of the polymer matrix. In specific embodiments, the polymer matrix comprises about 30% by weight methylphenidate, based on the total dry weight of the polymer matrix.

In accordance with any of the embodiments described herein, the composition may include from about 20 to about 225 mg per unit of methylphenidate base or an equivalent amount of a pharmaceutically acceptable salt thereof.

Non-Reactive Acrylic Polymers

Methylphenidate, including methylphenidate base in particular, is unstable and undergoes degradation in the presence of reactive functional groups, such as active hydrogen atoms or functional groups with hydrogen atoms available for chemical reaction or interaction with methylphenidate, such as, for example, carboxyl, hydroxyl, amine, thiol or silanol groups, which may be present in polymers, enhancers, excipients and other components that typically may be used in transdermal compositions. Major degradants of methylphenidate include ritalinic acid and erythol isomer, whose concentrations increase significantly with increasing amounts (by weight) of functional groups. Such degradation can greatly reduce the amount of the active species present in a composition after storage, thus reducing the amount of active methylphenidate available for drug delivery.

Polymer matrix compositions comprising acrylic polymers are known. In the context of transdermal methylphenidate compositions, polymer matrices including a blend of a non-functional, hydroxy functional, or minimally acid functional acrylic polymer and a silicone polymer, such as so-called "capped" or "amine-compatible" silicone PSAs, have been described. See, e.g., U.S. Pat. No. 6,210,705; U.S. Pat. No. 6,348,211; and U.S. Published Application 2008/0008746. The commercial product marketed under the name Daytrana® includes a polymer matrix comprising an acrylic polymer, a silicone polymer, and methylphenidate. This product suffers from the problem of "tight release," e.g., it can be difficult to remove the release liner from the polymer matrix without damaging the polymer matrix, rendering the product unsuitable for use. This problem has led to several Daytrana® product recalls. As discussed below, it surprisingly has been discovered that the compositions described herein do not suffer from the problem of tight release.

In some embodiments, the polymer matrices of the compositions described herein consist essentially of methylphenidate (in any form discussed above) and at least one non-reactive acrylic polymer. In this context "consist essentially of" means that the matrices are substantially free of another polymer, such as an acid-functional acrylic polymer, hydroxy-functional acrylic polymer, silicone polymer, a polyisobutylene polymer, polyvinylpyrrolidone (PVP), and other polymers with reactive functional groups that are known for use as carriers for transdermal compositions.

As used herein, the term "non-reactive acrylic polymer" includes any acrylic-type of polymers comprised of monomers that do not include functional groups reactive with methylphenidate, such as acid-functional or hydroxy-functional groups, as discussed above. Non-reactive acrylic polymers include those formed from acrylic esters copolymerized with other monomers that do not include groups that are reactive with methylphenidate. Non-reactive acrylic polymers include homopolymers, copolymers, terpolymers, etc., of esters or amides of acrylic-type carboxylic acids.

Suitable acrylic polymers can be obtained commercially or by polymerizing or copolymerizing suitable monomers such as acrylic monomers and other polymerizable monomers. Acrylate monomers which can be used include alkyl acrylates and alkyl methacrylates, such as methyl acrylate, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate, and amide-group containing-monomers, such as octyl acrylamide. In specific embodiments, the non-reactive acrylic polymer includes methyl acrylate monomers and 2-ethylhexyl acrylate monomers. In other specific embodiments the non-reactive acrylic polymer includes methyl methacrylate monomers, 2-ethylhexyl acrylate monomers, butyl acrylate monomers and amide-group containing monomers.

In some embodiments, the non-reactive acrylic polymer component of the polymer matrix consists of a single non-reactive acrylic polymer. In other embodiments, the non-reactive acrylic polymer component of the polymer matrix comprises a blend of a first non-reactive acrylic polymer and a second non-reactive acrylic polymer, and optionally includes additional (e.g., a third or more) non-reactive acrylic polymers.

Suitable non-reactive acrylic polymers which are commercially available include those sold by Henkel (Dusseldorf, Germany), under the Duro-Tak® brand such as Duro-Tak 87-900A, 87-901A, 87-9085, 87-9088, 87-9301A, and those sold by Cytec (Springfield, Mass.) under Gelva® Multipolymer Solution (Gelva® GMS) brand, such as Gelva GMS 3067, 3071, 3083, 3087 and Gelva 3235. Other suitable acrylic polymers are known in the art. See, e.g., the non-reactive acrylic polymers described in Satas, "Acrylic Adhesives, HANDBOOK OF PRESSURE-SENSITIVE ADHESIVE TECHNOLOGY, 2nd ed., pp. 396-456 (D. Satas, ed.), Van Nostrand Reinhold, N.Y. (1989); "Acrylic and Methacrylic Ester Polymers," POLYMER SCIENCE AND ENGINEERING, Vol. 1, 2nd ed., pp 234-268, John Wiley & Sons, (1984).

When the acrylic polymer component includes more than one non-reactive acrylic polymer, the polymers can be present in any ratio that results in a product with satisfactory physical and pharmacokinetic properties. For example, the acrylic polymer component can include from 0-100% of a first non-reactive acrylic polymer and from 100-0% of a second non-reactive acrylic polymer, based on the total dry weight of the acrylic component, including about 10 to about 90%, about 15-about 85%, about 20 to about 80%, about 25 to about 75%, about 33 to about 66%, and about 50% of the first non-reactive acrylic polymer, and the balance being the second (or third, etc.) non-reactive acrylic polymer(s). In specific embodiments, the acrylic polymer component includes about 80%, about 87%, or 100% of a first non-reactive acrylic polymer, and about 20%, about 13% and 0% of a second non-reactive acrylic polymer.

As noted above, in some embodiments, the polymer matrices of the compositions described herein consist essentially of methylphenidate or pharmaceutically acceptable salt thereof and at least one non-reactive acrylic polymer, although such compositions may include other non-polymer components that do not degrade the physical and/or pharmacokinetic properties of the compositions to pharmaceutically unacceptable levels. Generally, for polymer matrices that include methylphenidate in an amount from about 1% to about 50%, including from about 5% to about 40%, such as from about 10% to about 35%, or 30%, or 25%, or 20%, by weight, based on the total dry weight of the polymer matrix, the one or more non-reactive acrylic polymers will constitute from about 99% to about 50%, including from about 95% to about 60%, such as from about 90% to about 65%, or 70%, or 75%, or 80%, by weight of the polymer matrix, based on the total dry weight of the polymer matrix, with this number being adjusted to account for any excipients. In specific embodiments, the polymer matrix comprises about 70% by weight of one or more non-reactive acrylic polymers, based on the total dry weight of the polymer matrix. In specific embodiments, the polymer matrix comprises about 75% by weight of one or more non-reactive acrylic polymers, based on the total dry weight of the polymer matrix. In specific embodiments, the polymer matrix comprises about 80% by weight of one or more non-reactive acrylic polymers, based on the total dry weight of the polymer matrix.

Methods of Manufacture

Any of the compositions described herein may include a drug impermeable backing layer or film, adjacent one face of the polymer matrix. When present, the backing layer protects the polymer matrix from the environment and prevents loss of the drug and/or release of other components to the environment during use. Materials suitable for use as backing layers are well-known known in the art and can comprise films of polyester, polyethylene, vinyl acetate resins, ethylene/vinyl acetate copolymers, polyvinyl chloride, polyurethane, and the like, metal foils, non-woven fabric, cloth and commercially available laminates. A typical backing material has a thickness in the range of 2 to 1000 micrometers. Suitable backing materials include commercially available backings films, such as breathable backings such as 3M CoTran™ backings which feature low moisture vapor transmission rate and high oxygen transmission, and non-breathable polyester-based laminate backings such as 3M Scotchpak® backings (3M, St. Paul, Minn.), such as Scotchpak 9732 (3M, St. Paul, Minn.).

Additionally or alternatively, any of the compositions described herein may include a release liner, typically located adjacent the opposite face of the system as compared to the backing layer. When present, the release liner is removed from the system prior to use to expose the polymer matrix layer prior to topical application. Materials suitable for use as release liners are well-known known in the art and commercially available, such as silicone-coated polyester, polyethylene, polypropylene, and polystyrene release liners, such as those supplied by Loparex, (Cary, N.C.), such as those supplied under the under the PRIMELINER™ brand, and fluoro-coated polyester release liners supplied by 3M (St. Paul, Minn.), such as 3M Scotchpak™ fluoropolymer-coated polyester release liners.

The compositions described herein can be prepared by methods known in the art. As one step, the polymer matrices described herein can be prepared by methods known in the art, such as blending (mixing) the at least one non-reactive acrylic polymer(s) in powder or liquid form with an appropriate amount of drug in the presence of an appropriate solvent, such as a volatile organic solvent, optionally with other excipients. To form a final product, the drug/polymer/solvent mixture may be cast onto a release liner (optionally, at ambient temperature and pressure) followed by evaporation of the volatile solvent(s), for example, at room temperature, slightly elevated temperature, or by a heating/drying step, to form the drug-containing polymer matrix on a release liner. A backing layer may be applied to form a final product.

In accordance with any of the embodiments of the compositions described herein, the coat weight of the polymer matrix can be, in some embodiments, from about 3 mg/cm$^2$ to about 20 mg/cm$^2$, based on the active surface area of the polymer matrix. Exemplary coat weights include about 3 mg/cm$^2$, about 4 mg/cm$^2$, about 5 mg/cm$^2$, about 5.5 mg/cm$^2$, about 6 mg/cm$^2$, about 6.5 mg/cm$^2$, about 7 mg/cm$^2$, about 7.5 mg/cm$^2$, about 8 mg/cm$^2$, about 8.5 mg/cm$^2$, about 9 mg/cm$^2$, about 9.5 mg/cm$^2$, about 10 mg/cm$^2$, about 12 mg/cm$^2$, about 15 mg/cm$^2$, about 17 mg/cm$^2$, and about 20 mg/cm$^2$. In specific embodiments the coat weight of the polymer matrix is about 5.0 mg/cm$^2$, such as about 5.0 to about 6.0 mg/cm², including about 5.5 mg/cm², based on the active surface area of the of the polymer matrix.

In accordance with any of the embodiments of the compositions described herein, the methylphenidate can be present, in some embodiments, in an amount from about 0.5 mg/cm² to about 3 mg/cm², based on the active surface area of the of the polymer matrix. Exemplary amounts include about 0.5 mg/cm², about 0.8 mg/cm², about 1 mg/cm², about 1.2 mg/cm², about 1.4 mg/cm², about 1.6 mg/cm², about 1.7 mg/cm², about 1.8 mg/cm², about 2.0 mg/cm², about 2.2 mg/cm², about 2.4 mg/cm², about 2.6 mg/cm², about 2.8 mg/cm², and about 3.0 mg/cm². In specific embodiments, the methylphenidate is present in an amount of about 1.65 mg/cm² based on the active surface area of the polymer matrix.

An exemplary general method for preparing a unit final product of a composition as described herein in a flexible, finite form, is as follows:

1. Appropriate amounts of one or more non-reactive acrylic polymers, solvent(s) and/or co-solvent(s), and optional excipient(s) are combined and thoroughly mixed together in a vessel.
2. The methylphenidate is added to the mixture and agitation is carried out until the drug is uniformly mixed therein.
3. The composition is transferred to a coating operation where it is coated onto a release liner at a controlled specified thickness. The coated composition is then passed through an oven in order to drive off all volatile processing solvents.
4. The composition coated on the release liner is then brought into contact with a backing layer and wound into rolls.
5. Appropriate size and shape delivery systems are die-cut from the roll material and then pouched.

The order of steps, the amount of the ingredients, and the amount and time of agitation or mixing may be important process variables which will depend on the specific polymers, active agents, solvents and/or cosolvents, and optional excipients used in the composition, but these factors can be adjusted by those skilled in the art. The order in which each method step is performed can be changed if needed without detracting from the invention.

In accordance with any of the embodiments of compositions described herein, the size of the final product is, in some embodiments, in the range of from about 2 cm² to about 60 cm², including 12.5 cm², 14.5 cm², 15 cm², 18.75 cm², 22.5 cm², 25 cm², 30 cm², 37.5 cm², and 45 cm².

Methods of Use

The compositions described herein are useful in methods for the transdermal delivery of methylphenidate, including in methods for treating attention deficit disorder and/or attention deficit/hyperactivity disorder, postural orthostatic tachycardia syndrome, and narcolepsy. In such embodiments, a composition comprising a therapeutically effective amount of methylphenidate as described herein is topically applied to a subject in need thereof.

In some embodiments, the compositions achieve transdermal delivery of methylphenidate over a period of time of at least about 8 hours, including a period of time of at least about 8 hours to at least about 12 hours. In some embodiments, the compositions achieve transdermal delivery of methylphenidate over a period of time of about 8 hours, about 9 hours, about 10 hours, or longer, including up to and including about 24 hours. In some embodiments, the compositions are formulated for daily application.

The compositions described herein achieve a transdermal flux of methylphenidate (or a pharmaceutically acceptable salt thereof) that is sufficient to have a therapeutic effect. As used herein, "flux" (also called "permeation rate") is defined as the absorption of a drug through skin or mucosal tissue, and is described by Fick's first law of diffusion:

$$J = -D \, (dCm/dx)$$

where J is the flux in g/cm²/sec, D is the diffusion coefficient of the drug through the skin or mucosa in cm²/sec and dCm/dx is the concentration gradient of the drug across the skin or mucosa. In some embodiments the compositions described herein achieve a transdermal flux of methylphenidate (or a pharmaceutically acceptable salt thereof) of from at least about 0.05 mg/cm²/hour up to about 0.1 mg/cm²/hour, including about 0.07 mg/cm²/hour. In some embodiments, such a flux is achieved over a period of time of at least about 8 hours, about 9 hours, about 10 hours, or longer.

In accordance with other embodiments, there are provided compositions as described herein for use in the transdermal delivery of methylphenidate, such as for use by topically application to the skin or mucosa of a subject in need thereof, such as for treating ADD or ADHD, postural orthostatic tachycardia syndrome, or narcolepsy.

The following specific examples are included as illustrative of the compositions described herein. These example are in no way intended to limit the scope of the invention. Other aspects of the invention will be apparent to those skilled in the art to which the invention pertains.

Example 1

A polymer matrix composition is prepared with the following components, based on the dry weight of the polymer matrix:

60% by weight of a pressure-sensitive acrylic polymer comprised of 50% methyl acrylate monomers (MA) and 50% 2-ethylhexyl acrylate monomers (2-EHA)

15% by weight of a pressure-sensitive acrylic polymer comprised of methyl methacrylate monomers (MMA), 2-EHA monomers, butyl acrylate monomers (BA) and amide group-containing monomers 25% by weight methylphenidate base Example 2

A polymer matrix composition is prepared with the following components, based on the dry weight of the polymer matrix:

65% by weight of a pressure-sensitive acrylic polymer comprised of 80% MA monomers and 20% 2-EHA monomers 10% by weight of a pressure-sensitive acrylic polymer comprised of MMA monomers, 2-EHA monomers, BA monomers, and amide group-containing monomers 25% by weight methylphenidate base Example 3

A polymer matrix composition is prepared with the following components, based on the dry weight of the polymer matrix:

60% by weight of a pressure-sensitive acrylic polymer comprised of 80% MA monomers and 20% 2-EHA monomers 15% by weight of a pressure-sensitive acrylic polymer comprised of 50% MA monomers and 50% 2-EHA monomers 25% by weight methylphenidate base

Example 4

A polymer matrix composition is prepared with the following components, based on the dry weight of the polymer matrix:

75% by weight of a pressure-sensitive acrylic polymer comprised of 80% MA monomers and 20% 2-EHA monomers 25% by weight methylphenidate base

Example 5

A polymer matrix composition is prepared with the following components, based on the dry weight of the polymer matrix:

65% by weight of a pressure-sensitive acrylic polymer comprised of 80% MA monomers and 20% 2-EHA monomers 5% by weight of a pressure-sensitive acrylic polymer comprised of 50% MA monomers and 50% 2-EHA monomers 30% by weight methylphenidate base

Example 6

The polymer matrix compositions of Example 1-4 are coated on a release liner at a coat weight of 6.6 mg/cm$^2$ and provided with a backing layer, resulting in compositions in flexible, finite form with a methylphenidate content of 1.65 mg/cm$^2$.

The polymer matrix composition of Example 5 is coated on a release liner at a coat weight of 5.5 mg/cm$^2$ and provided with a backing layer, resulting in compositions in flexible, finite form with a methylphenidate content of 1.65 mg/cm$^2$.

Example 7

The flexible, finite forms of Example 6 are packaged in suitable packaging material and stored under typical storage conditions. After a period of time, the flexible, finite forms are removed from the packaging material and the release liners are removed. The release liners can be removed easily, without causing any damage to the polymer matrix layer.

Table 1 below sets forth the average peel (n=3) from the release liner over storage time (0-9 months) at ambient temperatures of the compositions of Example 6 (prepared as 1.4"×1.4" rounded square units), based on the matrix compositions of Examples 1-5, as compared to a composition based on the commercial Daytrana® product. The results are presented in g/unit.

| Composition | T = 0 | 1M | 2M | 3M | 4M | 5M | 6M | 9M |
|---|---|---|---|---|---|---|---|---|
| Example 1 | 15 | 20 | 17 | 22 | 26 | 25 | 25 | 33 |
| Example 2 | 15 | 10 | 13 | 19 | 22 | 22 | 16 | 11 |
| Example 3 | 8 | 9 | 12 | 14 | 17 | 17 | 15 | 17 |
| Example 4 | 24 | 24 | 23 | 30 | 27 | 27 | 26 | 18 |
| Example 5 | 12 | 15 | 15 | 15 | 16 | 16 | 14 | 15 |
| Daytrana (lab Preparation) | 17 | 37 | 59 | 59 | 169 | 173 | 213 | 229 |

These results show that the compositions described herein do not suffer from the problem of tight release that is observed with the commercial Daytrana® product. These results are surprising and unexpected in view of the persistent problem of tight release experienced with the commercial Daytrana® product.

Example 8

A Phase I, randomized, single dose, three-way crossover study was conducted in 15 subjects to assess the relative bioavailability of methylphenidate from two compositions as described herein as compared to the commercially availably methylphenidate product Daytrana®.

Treatment A:

Flexible, finite forms having a size of 54 cm$^2$ were prepared using the polymer matrix according to Example 3 (25% methylphenidate; 15% Gelva 3087; 60% Gelva 3235) applied at a coat weight of about 6.0 mg/cm$^2$ (based on the total weight of the matrix) to provide about 81.0 mg methylphenidate per unit dosage form.

Treatment B:

Flexible, finite forms having a size of 45 cm$^2$ were prepared using the polymer matrix according to Example 5 (30% methylphenidate; 5% Gelva 3087; 65% Gelva 3235) applied at a coat weight of about 5.5 mg/cm$^2$ (based on the total weight of the matrix) to provide about 74.3 mg methylphenidate per unit dosage form.

Treatment C:

A 37.5 cm$^2$ Daytrana® patch comprising 82.5 mg methylphenidate per unit dosage form.

For each treatment period, the unit dosage form was applied for 9 hours. Treatment periods were separated by a wash-period of at least 7 days. Blood samples were collected pre-treatment, at hours 1, 2, 4, 6, 8, and 9 of treatment (prior to patch removal), and at 10, 24, and 36 hours post-treatment (after patch removal) and analyzed for methylphenidate plasma concentration. The amount of methylphenidate released from each patch was assessed by measuring the amount of methylphenidate remaining after removal.

Following each treatment, plasma concentrations of d-methylphenidate, l-methylphenidate and combined d-, l-methylphenidate started to gradually increase following a 2 hour lag time, and continued to increase following patch removal at 9 hours. After reaching Tmax at around 10 hours, plasma concentrations of d-methylphenidate, l-methylphenidate and combined d-,l-methylphenidate started to decrease, and by 36 hours after patch application they were around the lower limits of quantitation (0.05 ng/mL for d-methylphenidate and 0.01 ng/mL for l-methylphenidate).

Results:

Combined d-, l-methylphenidate plasma concentrations after Treatments A and B were comparable to those of Treatment C. The pharmacokinetic parameters Cmax, AUC (0-t) and AUC(0-inf) for combined d-, l-methylphenidate for both Treatments A and B also were comparable to those of the reference Treatment C. The relative bioavailabilities of treatments A and B, based on the AUC(0-inf) of combined d-, l-methylphenidate, were 1.11 (90% CI: 1.015-1.221) and 1.01 (90% CI: 0.924-1.112), respectively, in comparison with Treatment C. The mean absolute amount and the percentage of applied dose absorbed from the patch compared to control were 17.18 mg and 20.5%, 16.22 mg and 21.3%, and 14.17 mg and 18.0% for Treatments A, B, and C, respectively. The three treatments had similar dermal wear characteristics and were well-tolerated; the safety profiles of the three treatments were similar.

These results show that the compositions described herein can achieve comparable drug delivery and pharmacokinetic profiles as compared to the commercial Daytrana® product.

What is claimed is:

1. A composition for the transdermal delivery of methylphenidate in the form of a flexible finite system for topical application consisting of a backing layer, a single skin-contacting polymer matrix layer, and, optionally, a release liner layer, wherein:
   the single skin-contacting polymer matrix layer consists essentially of:
   (a) methylphenidate and/or a pharmaceutically acceptable salt thereof; and
   (b) at least one non-reactive acrylic polymer that is polymerized from monomers including one or more monomers selected from the group consisting of methyl acrylate, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, and amide group-containing monomers,
   wherein the polymer matrix is free of polymers with reactive functional groups and is free of silicone polymers.

2. The composition as claimed in claim 1, wherein the polymer matrix layer consists essentially of a first non-reactive acrylic polymer and said methylphenidate and/or pharmaceutically acceptable salt thereof.

3. The composition as claimed in claim 1, wherein the polymer matrix layer consists essentially of a first non-reactive acrylic polymer, a second non-reactive acrylic polymer, and, optionally, additional non-reactive acrylic polymers, and said methylphenidate and/or pharmaceutically acceptable salt thereof.

4. The composition as claimed in claim 1, wherein at least one non-reactive acrylic polymer is polymerized from monomers including methyl acrylate and 2-ethylhexyl acrylate monomers.

5. The composition as claimed in claim 1, wherein at least one non-reactive acrylic polymer is polymerized from monomers including amide group-containing monomers.

6. The composition as claimed in claim 1, wherein at least one non-reactive acrylic polymer is polymerized from monomers including methyl methacrylate, 2-ethylhexyl acrylate, butyl acrylate monomers and amide group-containing monomers.

7. The composition as claimed in claim 1, wherein the polymer matrix layer consists essentially of (a) first non-reactive acrylic polymer that is polymerized from 50% methyl acrylate monomers and 50% 2-ethylhexyl acrylate monomers, based on the weight of the first acrylic polymer; (b) a second non-reactive acrylic polymer that is polymerized from monomers including methyl methacrylate monomers, 2-ethylhexyl acrylate monomers, butyl acrylate monomers, and amide group-containing monomers, and (c) methylphenidate and/or a pharmaceutically acceptable salt thereof.

8. The composition as claimed in claim 7, wherein the polymer matrix layer consists of 60% by weight of said first non-reactive acrylic polymer, 15% by weight of said second non-reactive acrylic polymer, and 25% by weight methylphenidate, based on the total dry weight of the polymer matrix.

9. The composition as claimed in claim 1, wherein the polymer matrix layer consists essentially of (a) first non-reactive acrylic polymer that is polymerized from 80% methyl acrylate monomers and 20% 2-ethylhexyl acrylate monomers, based on the weight of the first acrylic polymer; (b) a second non-reactive acrylic polymer that is polymerized from monomers including methyl methacrylate monomers, 2-ethylhexyl acrylate monomers, butyl acrylate monomers and amide group-containing monomers and (c) methylphenidate and/or a pharmaceutically acceptable salt thereof.

10. The composition as claimed in claim 9, wherein the polymer matrix layer consists of 65% by weight of said first non-reactive acrylic polymer, 10% by weight of said second non-reactive acrylic polymer, and 25% by weight methylphenidate, based on the total dry weight of the polymer matrix.

11. The composition as claimed in claim 1, wherein the polymer matrix layer consists essentially of (a) first non-reactive acrylic polymer that is polymerized from 80% methyl acrylate monomers and 20% 2-ethylhexyl acrylate monomers, based on the weight of the first acrylic polymer; (b) a second non-reactive acrylic polymer that is polymerized from 50% methyl acrylate monomers and 50% 2-ethylhexyl acrylate monomers, based on the weight of the second acrylic polymer and (c) methylphenidate and/or a pharmaceutically acceptable salt thereof.

12. The composition as claimed in claim 11, wherein the polymer matrix layer consists of 60% by weight of said first non-reactive acrylic polymer, 15% by weight of said second non-reactive acrylic polymer, and 25% by weight methylphenidate.

13. The composition as claimed in claim 11, wherein the polymer matrix layer consists of 65% by weight of said first non-reactive acrylic polymer, 5% by weight of said second non-reactive acrylic polymer, and 30% by weight methylphenidate.

14. The composition as claimed in claim 1, wherein the polymer matrix layer consists essentially of (a) a non-reactive acrylic polymer that is polymerized from 80% methyl acrylate monomers and 20% 2-ethylhexyl acrylate monomers, based on the weight of the acrylic polymer and (b) methylphenidate and/or a pharmaceutically acceptable salt thereof.

15. The composition as claimed in claim 14, wherein the polymer matrix layer consists of 75% by weight of said non-reactive acrylic polymer, and 25% by weight methylphenidate.

16. The composition as claimed in claim 1, wherein the polymer matrix layer has a coat weight of about 4-7 mg/cm$^2$ based on the active surface area of the polymer matrix.

17. The composition as claimed in claim 1, wherein the polymer matrix layer has a coat weight of about 6.6 mg/cm$^2$ based on the active surface area of the polymer matrix.

18. The composition as claimed in claim 1, wherein the polymer matrix layer has a coat weight of about 5.5 mg/cm$^2$ based on the active surface area of the polymer matrix.

19. The composition as claimed in claim 1, comprising a methylphenidate content of about 0.5-3 mg/cm$^2$ based on the active surface area of the polymer matrix layer.

20. The composition as claimed in claim 1, comprising a methylphenidate content of about 1.65 mg/cm$^2$ based on the active surface area of the polymer matrix layer.

21. The composition as claimed in claim 1, comprising 20-30% by weight methylphenidate, based on the weight of the polymer matrix layer.

22. The composition as claimed in claim 1, wherein said composition delivers methylphenidate over a period of time of at least about 8-12 hours.

23. A method for the transdermal delivery of methylphenidate, comprising topically applying a composition as claimed in claim 1 to the skin or mucosa of a subject in need thereof.

24. A method of making a composition for the transdermal delivery of methylphenidate in the form of a flexible finite system for topical application consisting of a backing layer, a single skin-contacting polymer matrix layer, and, optionally, a release liner layer, comprising forming a single skin-contacting polymer matrix consisting essentially of:
(a) methylphenidate and/or a pharmaceutically acceptable salt thereof; and
(b) at least one non-reactive acrylic polymer polymerized from monomers including one or more monomers selected from the group consisting of methyl acrylate, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, and amide group-containing monomers,
by a process comprising admixing the methylphenidate and/or pharmaceutically acceptable salt thereof with the at least one non-reactive acrylic polymer,
wherein the polymer matrix is free of polymers with reactive functional groups and is free of silicone polymers.

25. The composition as claimed in claim 1, wherein the flexible finite system includes the optional release liner layer.

26. The composition as claimed in claim 1, wherein the flexible finite system does not include the optional release liner layer.

* * * * *